(12) United States Patent
Friend et al.

(10) Patent No.: US 6,973,388 B2
(45) Date of Patent: Dec. 6, 2005

(54) METHODS OF DIAGNOSING DISEASE STATES USING GENE EXPRESSION PROFILES

(75) Inventors: Stephen H. Friend, Seattle, WA (US); Roland Stoughton, San Diego, CA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 301 days.

(21) Appl. No.: 09/783,474

(22) Filed: Feb. 14, 2001

(65) Prior Publication Data

US 2001/0018182 A1 Aug. 30, 2001

Related U.S. Application Data

(63) Continuation of application No. 09/334,328, filed on Jun. 16, 1999, now Pat. No. 6,218,122.
(60) Provisional application No. 60/090,004, filed on Jun. 19, 1998.

(51) Int. Cl.[7] ............... G01N 33/48; C12Q 1/68; C12P 21/06; G06G 7/48
(52) U.S. Cl. ............... 702/19; 435/6; 435/69.1; 703/11
(58) Field of Search ............... 435/6, 69.1, 4, 435/7.1, 7.2; 703/11; 702/19, 20, 27

(56) References Cited

U.S. PATENT DOCUMENTS

| 5,464,742 A | * 11/1995 | Swift et al. ............... 435/6 |
| 5,510,270 A | 4/1996 | Fodor et al. ............... 436/518 |
| 5,556,752 A | 9/1996 | Lockhart et al. ............... 435/6 |
| 5,569,588 A | 10/1996 | Ashby et al. ............... 435/6 |
| 5,578,832 A | 11/1996 | Trulson et al. ............... 250/458.1 |
| 5,633,161 A | 5/1997 | Shyjan ............... 435/325 |
| 5,663,071 A | 9/1997 | Zetter et al. ............... 435/325 |

(Continued)

FOREIGN PATENT DOCUMENTS

| EP | 0 534 858 A1 | 9/1992 |
| WO | WO 97/10365 | 3/1997 |
| WO | WO 98/07888 | 2/1998 |
| WO | WO 98/24935 | 6/1998 |
| WO | WO 98/41531 | 9/1998 |

OTHER PUBLICATIONS

"Tumor Markers", National Cancer Institute, accessed Jun. 5, 1998, modified 4/98. http://cancernet.nci.nih.gov/clinpdq/detection/Tumor_Markers. html.

(Continued)

*Primary Examiner*—Ardin H. Marschel
(74) *Attorney, Agent, or Firm*—Jones Day

(57) ABSTRACT

The present invention provides methods for monitoring disease states in a subject, as well as methods for monitoring the levels of effect of therapies upon a subject having one or more disease states. The methods involve: (i) measuring abundances of cellular constituents in a cell from a subject to obtain a diagnostic profile, (ii) measuring abundances of cellular constituents in a cell of one or more analogous subjects to obtain perturbation response profiles which correlate to a particular disease or therapy, and (iii) determining the interpolated perturbation response profile or profiles which best fit the diagnostic profile. In other aspects, the invention also provides a computer system capable of performing the methods of the invention, databases comprising perturbation response profiles for one or more diseases and/or therapies, and kits for determining levels of disease states and/or therapeutic effects according to the methods of the invention.

9 Claims, 4 Drawing Sheets

U.S. PATENT DOCUMENTS

| | | | |
|---|---|---|---|
| 5,674,739 A | 10/1997 | Shyjan | 435/252.3 |
| 5,677,125 A | 10/1997 | Holt et al. | 435/6 |
| 5,695,937 A | 12/1997 | Kinzler et al. | 435/6 |
| 5,702,902 A | 12/1997 | Tartaglia | 435/6 |
| 5,707,807 A | 1/1998 | Kato | 435/6 |
| 5,721,337 A | 2/1998 | Zetter et al. | 530/300 |
| 5,721,351 A | 2/1998 | Levinson | 536/23.4 |
| 5,723,290 A | 3/1998 | Eberwine et al. | 435/6 |
| 5,738,998 A | 4/1998 | Deth | |
| 5,741,666 A | 4/1998 | Tartaglia | 435/69.1 |
| 5,746,204 A | 5/1998 | Schauss | 128/630 |
| 5,756,310 A | 5/1998 | Bandman et al. | |
| 5,759,776 A | 6/1998 | Smith et al. | 435/6 |
| 5,935,060 A | 8/1999 | Iliff | 600/300 |
| 5,965,352 A | 10/1999 | Stoughton et al. | 435/4 |
| 6,132,969 A | 10/2000 | Stoughton et al. | 435/6 |
| 6,146,830 A | 11/2000 | Friend et al. | 435/6 |
| 6,165,709 A | 12/2000 | Friend et al. | 435/4 |
| 6,218,122 B1 | 4/2001 | Friend et al. | 435/6 |
| 6,222,093 B1 | 4/2001 | Marton et al. | 800/3 |
| 6,267,722 B1 * | 7/2001 | Anderson et al. | 600/300 |
| 6,324,479 B1 | 11/2001 | Friend et al. | 702/19 |

OTHER PUBLICATIONS

"Adult Primary Liver Cancer", National Cancer Institute, accessed Jun. 5, 1998, modified 6/98, http://cancernet.nci.nih.gov/ clinpdq/soa/ Adult_primary_liver_cancer_Physician.html.

"Ovarian Germ Cell Tumor", National Cancer Institute, accessed Jun. 5, 1998, modified 10/97, http://cancernet.nci.nih.gov/clinpdq/soa/Ovarian_germ_cell_tumor_Physician.html.

"Huntington's Disease: Hope through Rersearch", National Institute of Neurological Disorders and Stroke, accessed Jun. 19, 1998; updated Apr. 7, 1998; http://www.intelihealth . . . /ihtlH?d=dmtJHE&c=36290&p=~ br, IHW . . . .

"The Neurofibromatoses", National Institute of Neurological Disorders and Stroke, accessed Jun. 19, 1998; updated May, 1997, http://www.intelihealth . . . /ihtlH?d=dmtJHE&c=36296&p=~br, IHW . . . .

"Tay–Sachs Disease", National Institute of Neurological Disorders and Stroke, accessed Jun. 19, 1998; updated Apr. 4, 1997; http://www.intelihealth . . . /ihtlH?d=dmtJHE&c=36308&p=~br, IHW . . . .

"Polycystic Kidney Disease", National Institute of Diabetes and Digestive and Kidney Diseases, accessed Jun. 19, 1998, updated Mar. 11, 1998, www.niddk.nih.gov/health/kidney/pubs/polycyst/polycyst.htm.

Blanchard et al., 1996, "High–density oligonucleotide arrays", Biosensors & Bioelectronics 11:687–690.

Blanchard and Hood, 1996, "Sequence to array: probing the genome's secrets", Nature Biotechnol. 14:1649.

Brecher et al., 1996, "Coagulation protein function. IV. Effect of acetaldehyde upon factor X and factor Xa, the proteins at the gateway to the common coagulation pathway", Alcohol 13:539–545.

Burnette, 1981, "Western blotting: electrophoretic transfer of proteins from sodium dodecyl sulphate–polyacrylamide gels to unmodified nitrocellulose and radiographic detection with antibody and radioiodinated protein A", Anal. Biochem. 112:195–203.

Chang et al., 1998, "Cloning, expression, and characterization of mouse tissue factor pathway inhibitor (TFPI)", Thromb. Haemost. 79:306–309.

Csendes, 1989, "An interval method for bounding level sets of parameter estimation problems", Computing 41:75–86.

Cyert and Thorner, 1992, "Regulatory subunit (gene product) of yeast Ca2$^+$/calmodulin–dependent phosphoprotein phosphatases is required for adaptation to pheromone", Mol. Cell. Biol. 12:3460–3469.

Dackiw et al., 1996, "Integrin engagement induces monocyte procoagulant activity and tumor necrosis factor production via induction of tyrosine phosphorylation", J. Surg. Res. 64:210–215.

D'Ambra, 1997, "Restoration of the normal coagulation process: advances in therapies to antagonize heparin", J. Cardiovasc. Pharmacol. 27(Suppl 1):S58–62.

DeRisi et al., 1996, "Use of a cDNA microarray to analyse gene expression patterns in human cancer", Nature Genet. 14:457–460.

Deshaies et al., 1988, "A subfamily of stress proteins facilitates translocation of secretory and mitochondrial precursor polypeptides", Nature 332:800–805.

DiGuiseppi, "Screening for neural tube defects—including folic acid prophylaxis", Ch. 42 in NIH on–line publication entitled *Guide to Clinical Preventive Services,* accessed on Jun. 5, 1998. http://text.nlm.nih.gov/cps/www/cps.48.html.

El Harrouni et al. 1996, Boundary and parameter identification using genetic algorithms and boundary element method, Proceedings of the International Conference on Computer Methods and Water Resources, Computational Mechanics, Inc., Bellerica, MA, pp. 487–495.

Elisen et al., 1998, "Protein C acts as a procoagulant by inhibiting the thrombomodulin–induced activation of protein C in human plasma", Blood 91:1542–1547.

Esmon, 1995, "Thrombomodulin as a model of molecular mechanisms that modulate protease specificity and function at the vessel surface", FASEB J. 9:946–955.

Ferguson et al., 1996, "A fiber–optic DNA biosensor microarray for the analysis of gene expression", Nature Biotechnol. 14:1681–1684.

Fodor et al., 1991, "Light–directed, spatially addressable parallel chemical synthesis", Science 251:767–773.

Goffeau et al., 1996, "Life with 6000 genes", Science 274:546, 563–567.

Heller et al., 1997, "Discovery and analysis of inflammatory disease–related genes using cDNA microarrays", Proc. Natl. Acad. Sci. USA 94:2150–2155.

Izumi, et al., 1992, "Alpha–fetoprotein production by hepatocellular carcinoma is prognostic of poor patient survival", J. Surg. Oncol. 49:151–155.

Kalafatis et al., 1997, "The regulation of clotting factors", Crit. Rev. Eukaryot. Gene Expr. 7:241–280.

Lander, 1996, "The new genomics: global views of biology", Science 274:536–539.

Lockhart et al., 1996, "Expression monitoring by hybridization to high–density oligonucleotide arrays", Nature Biotechnol. 14:1675–1680.

Marubini and Resele, 1971, "Computer program for fitting the logistic and the Gompertz function to growth data", Computer Programs in Biomedicine 2:16–23.

Marx, "Familial Multiple Endocrine Neoplasia Type 1", National Institute of Diabetes and Digestive and Kidney Diseases, accessed Jun. 19, 1998, updated Mar. 11, 1998, www.niddk.nih.gov/health/wndo/pubs/fmen1/fmen1.htm.

Maskos and Southern, 1992, "Oligonucleotide hybridizations on glass supports: a novel linker for oligonucleotide synthesis and hybridization properties of oligonucleotides synthesized in situ", Nucl. Acids Res. 20:1679–1684.

Nakayama, 1997, "Furin: a mammalian subtilisin/Kex2p–like endoprotease involved in processing of a wide varity of precursor proteins", Biochem. J. 327:625–635.

Nalecz and Wojtczak, 1982, "Kinetic approach to the transport of branched chain α–ketoacids through biomembranes", in: *Transport in Biomembranes: Model Systems and Reconstitution,* Antolini et al., eds., Raven Press, New York, pp. 227–234.

Nguyen et al., 1995, "Differential gene expression in the murine thymus assayed by quantitative hybridization of arrayed cDNA clones", Genomics 29:207–216.

Pease et al., 1994, "Light–generated oligonucleotide arrays for rapid DNA sequence analysis", Proc. Natl. Acad. Sci. USA 91:5022–5026.

Piétu et al., 1996, "Novel gene transcripts preferentially expressed in human muscles revealed by quantitative hybridization of a high density cDNA array," Genome Res. 6:492–503.

Prashar and Weissman, 1996, "Analysis of differential gene expression by display of 3'end restriction fragments of cDNAs", Proc. Natl. Acad. Sci. USA 93:659–663.

Rouf and Alaoui, 1996, "Computation of dynamic electromagnetic problems using Lagrangian formalism and multidimensional $C^K$ spline functions", Z. Angew. Math. Mech. 76:513–514.

Sagliocco et al., 1996, "Identification of proteins of the yeast protein map using genetically manipulated strains and peptide–mass fingerprinting", Yeast 12:1519–1533.

Schena et al., 1995, "Quantitative monitoring of gene expression patterns with a complementary DNA microarray", Science 270:467–470.

Schena et al., 1996, "Parallel human genome analysis: microarray–based expression monitoring of 1000 genes", Proc. Natl. Acad. Sci. USA 93:10614–10619.

Shalon et al., 1996, "A DNA microarray system for analyzing complex DNA samples using two–color fluorescent probe hybridization", Genome Res. 6:639–645.

Shevchenko et al., 1996, "Linking genome and proteome by mass spectrometry: large–scale identification of yeast proteins from two dimensional gels", Proc. Natl. Acad. Sci. USA 93:14440–14445.

Thorsness et al., 1989, "Positive and negative transcriptional control by heme of genes encoding 3–hydroxy–3–methylglutaryl coenzyme A reductase in *Saccharomyces cerevisiae"*, Mol. Cell. Biol. 9:5702–5712.

Uthman, "Interpretation of Lab Test Profiles", pp. 1–15, accessed May 20, 1998 http://www.bookcase.com/library/faq/usenet/pathology/lab–test–interpretation.html.

Velculescu et al., 1995, "Serial analysis of gene expression", Science 270:484–487.

Yatscoff et al., 1996, "Pharmacodynamic monitoring of immunosuppressive drugs", Transpl. Proc. 28:3013–3015.

Zaldivar and Ghai, 1980, "Mathematical model of mean age, mean arsenic dietary dose and age–specific prevalence rate from endemic chronic arsenic poisoning: a human toxicology study", Zbl. Bakt. Hyg. I. Abt. Orig. B 170:402–408.

Zhao et al., 1995, "High–density cDNA filter analysis: a novel approach for large–scale, quantitative analysis of gene expression," Gene 156:207–213.

DeRisi et al., "Exploring the Metabolic and Genetic Control of Gene Expression on a Genomic Scale," Science, vol. 278, Oct. 24, 1997, pp. 680–686.

Zhang, et al., "Gene Expression Profiles in Normal and Cancer Cells," Science, vol. 276, May 23, 1997, pp. 1268–1272.

* cited by examiner

METHODS OF DIAGNOSING DISEASE STATES USING GENE EXPRESSION PROFILES

This application is a continuation of U.S. patent application Ser. No. 09/334,328, filed Jun. 16, 1999, now U.S. Pat. No. 6,218,122, which claims the benefit of U.S. Provisional Patent Application No. 60/090,004, filed on Jun. 19, 1998, each of which is incorporated herein by reference in its entirety.

1. FIELD OF THE INVENTION

The field of this invention relates to methods for determining or monitoring the progression of disease states or the efficacy of therapeutic regimens in a subject, preferably a human patient. In particular, the invention relates to methods for monitoring disease states or therapies at times and/or levels before changes in protein function or activity occur.

2. BACKGROUND

Within the past decade, several technologies have made it possible to monitor the expression level of a large number of transcripts within a cell at any one time (see, e.g., Schena et al., 1995, Quantitative monitoring of gene expression patterns with a complementary DNA micro-array, Science 270: 467–470; Lockhart et al., 1996, Expression monitoring by hybridization to high-density oligonucleotide arrays, Nature Biotechnology 14: 1675–1680; Blanchard et al., 1996, Sequence to array: Probing the genome's secrets, Nature Biotechnology 14, 1649; 1996, U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms, such as human, for which there is an increasing knowledge of the genome, it is possible to simultaneously monitor large numbers of the genes within the cell.

Early applications of transcript array technology have involved identification of genes which are up regulated or down regulated in various diseased states. Additional uses for transcript arrays have included the analyses of members of signaling pathways, and the identification of targets for various drugs. However, it has not previously been recognized that transcript arrays might be beneficial in monitoring the level of either disease states or effect of therapies therapies thereto. In particular, it has not been recognized that disease states and/or therapies might be monitored by using transcript arrays to detect compensatory changes that occur as a result of incipient, small changes in the activity of proteins due to perturbations from the disease state and/or therapy.

However, the identification of preliminary changes in biological pathways caused either by the actions of disease states or by therapeutic regimens, such as drug regimens, for disease states is a problem of great commercial and human importance. Most of the decisions that need to be made to run efficient clinical trials and to properly manage the health of patients rely on assays that monitor changes in cells in the body. For example, when physicians are following patients to determine if they have changes in organ function, such as in the kidney, liver, or heart, they rely on monitoring changes in enzymatic functions that can provide clues as to the cellular changes associated with various disease processes.

The ability to make correct therapeutic interventions therefore relies on the ability to have sensitive monitors of whether a patient has had changes in the physiology that have been impacted by disease or by therapy. Some of these needs are related to following particular protein activity levels. For example levels of alpha-fetoprotein (AFP) or alkaline phosphatase (ALP) are commonly used to monitor liver damage (see, e.g., Izumi, R. et al., 1992, Journal of Surgical Oncology 49: 151–155). The action of immunosuppressants Cyclosporin A and mycophalote mofetil have also been monitored using activity assays for the target enzymes calcineurin and inosine monophosphate, respectively (see, Yatscoff, R. W. et al., 1996, Transplantation Proceedings 28: 3013–3015). Other examples involve monitoring protein function in patients who have defects in the clotting pathway.

Thus, the power of being able to monitor changes in subjects by monitoring protein functions are well known in the art, and such techniques are widespread both in the detection of drug effects in animal trials, and in the detection of drug and disease effects in humans. It would be a significant benefit, however, to be able to monitor early changes in a cell that correlate with levels of a disease state or therapy and which precede detectable changes in actual protein function or activity. Such techniques would allow, for example, earlier diagnosis or prognosis or determination of the level of a disease state. In particular, the existence of such techniques would allow for determination of the level of a disease state (e.g., the stage or level of progression of a disease) in a subject before symptoms of the disease state can be observed. Earlier, more effective therapeutic intervention would then be possible. The ability to monitor such early changes in a cell resulting from therapy would likewise be of significant benefit, since therapeutic regimens could then be monitored and readily modified for maximum effectiveness.

Discussion or citation of a reference herein shall not be construed as an admission that such reference is prior art to the present invention.

3. SUMMARY OF THE INVENTION

The present invention provides methods for monitoring diseases or disease states in a subject. The methods of the invention involve comparing a "diagnostic profile", obtained by measuring RNA or protein abundances or activities in a cell of the subject, with "interpolated perturbation response profiles", which are obtained by measuring RNA or protein abundances or activities in a cell of an analogous subject or subjects at various levels of disease, i.e., at various levels of progression of the diseases or disease states being monitored.

The present invention also provides methods for monitoring the efficacy or response of therapy upon a subject. The methods involve comparing a diagnostic profile, obtained by measuring gene or protein abundances in cells from a subject undergoing a particular therapy, with interpolated perturbation response profiles which are obtained by measuring RNA or protein abundances or activities in cells of analogous subjects in response to known levels of therapeutic efficacy or response.

The present invention also provides a computer system for analyzing levels of disease states and or therapeutic efficacy according to the above methods.

The methods of the invention are based at least in part on the discovery that perturbations on various constituents of a cell, such as perturbations on protein function or activity, which occur as a result of a disease state or therapy result in characteristic changes in the transcription and activity of other genes, and that such changes can be used to define a "signature" of the particular alterations which are correlated with the progression of the particular disease state or therapy. This is true even if there is no actual disruption in the function or activity level of proteins associated with the disease state. Thus, the methods of the present invention are different from and independent of monitoring protein function. Further, the methods of the invention can be used to monitor several diseases and/or therapies simultaneously.

In more detail, the present invention provides, first, methods for determining or monitoring the level of one or more disease states (i.e., the progression of one or more disease states) upon a subject by: (i) obtaining a diagnostic profile by measuring abundances of cellular constituents in a cell from a subject known of suspected of having a disease state; (ii) obtaining interpolated perturbation response profiles for each disease state being monitored by, first, obtaining response profiles by measuring abundances of cellular constituents that occur in cells of an analogous subject or subjects at a plurality of levels of each disease state, and second, interpolating the thus obtained response profiles; and (iii) determining the interpolated perturbation response profile for each disease state for which similarity is greatest between the diagnostic profile and a combination of the determined interpolated response profiles, according to some objective measure. The level of a particular disease state is thereby indicated by the disease level correlated to the thus determined interpolated response profile for that disease state.

The present invention provides, second, methods for determining or monitoring the effect of one or more therapies upon a subject by: (i) obtaining a diagnostic profile by measuring abundances of cellular constituents in a cell from a subject undergoing one or more therapies, (ii) obtaining interpolated perturbation response profiles for each therapy being monitored by, first, obtaining response profiles by measuring abundances of cellular constituents that occur in cells of an analogous subject or subjects at a plurality of levels of effect of each therapy, and second, interpolating the thus obtained response profiles; and (iii) determining the interpolated perturbation response profile for each therapy for which similarity is greatest between the diagnostic profile and a combination of the determined interpolated response profiles, according to some objective measure. The effect of a particular therapy is thereby indicated by the level of effect correlated to the thus determined interpolated response profile for that therapy. In various aspects of this second embodiment, the methods of the invention can be used to monitor beneficial effects or adverse effects of therapies. For example, the methods can be used to monitor toxic effects of a therapy (e.g., one or more drugs or a chemotherapy).

The present invention further provides a computer system for analyzing levels of one or more disease states and/or the effect of one or more therapies upon a subject. The computer system comprises a processor, and memory coupled to said processor which encodes one or more programs. The programs encoded in memory cause the processor to perform the steps of the above methods wherein the diagnostic profiles and perturbation response profiles are received by the computer system as input.

In yet another embodiment, the invention also provides kits for determining the level of a disease state or the level of effect of a therapy. In still another embodiment, the invention provides databases comprising response profile data (i.e., response profiles) for one or more diseases or therapies which may be used in any of the above embodiments of the invention.

In various aspects of the above embodiments, the diagnostic profile can be determined by measuring gene expression, protein abundances, protein activities, or a combination of such measurements. In a preferred aspect of the above embodiments, the determined interpolated response profile for each disease state or therapy is the interpolated response profile which minimizes an objective function of the difference between the diagnostic profile and a combination of the determined interpolated response profiles for all disease states or therapies being evaluated.

4. BRIEF DESCRIPTION OF THE DRAWINGS

FIG. 1 illustrates exemplary responses of gene expression to the deletion of one of the two (diploid) copies of the SUN2 gene in the yeast *Saccharomyces cerevisiae*; $\log_{10}$ of the ratio of mRNA expression level in the deletion mutant to the expression level in the wild type strain is plotted on the vertical axis, vs. hybridization intensity, which is roughly proportional to molecular abundance of transcripts, on the horizontal axis; genes whose mRNA expression consistently increased or decreased in five repeated experiments are labeled, and flagged with error bars that indicate the standard deviation of the five repeated measurements.

FIG. 2 illustrates response curves of the 30 yeast genes, out of approximately 6000 measured yeast genes, that had the largest expression ratio changes to methotrexate drug exposure; methotrexate exposure levels were 3, 6, 25, 50, 100, and 200 $\mu$M; the 100 $\mu$M titration resulted in a 50% growth defect; responses have been set to zero at the arbitrary abscissa of –0.5.

5. DETAILED DESCRIPTION

Figure 1:
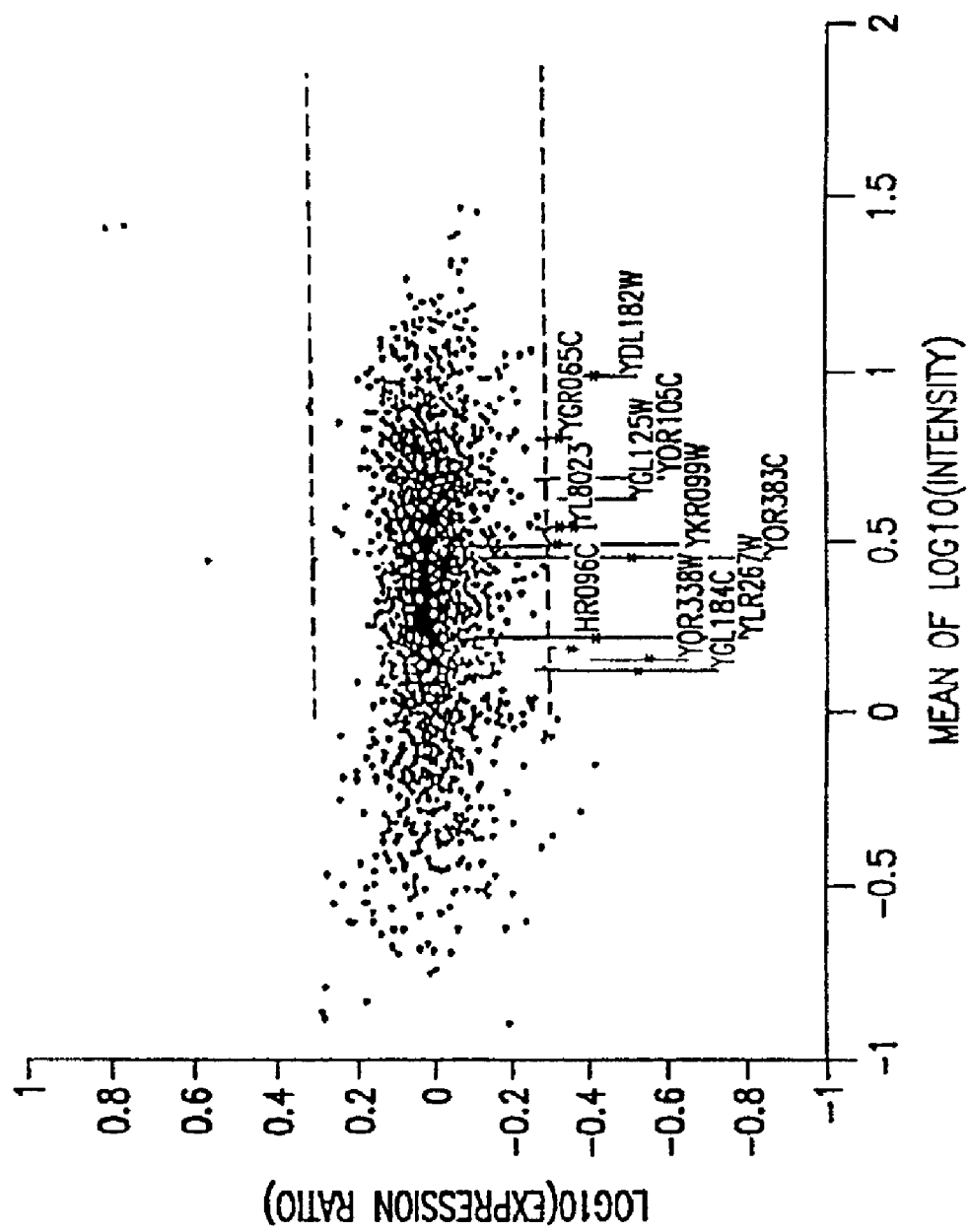

This section presents a detailed description of the present invention and its applications. This description is by way of several exemplary illustrations, in increasing detail and specificity, of the general methods of this invention. These examples are non-limiting, and related variants that will be apparent to one of skill in the art are intended to be encompassed by the appended claims. Following these examples are descriptions of embodiments of the data gathering steps that accompany the general methods.

5.1. Introduction

The present invention includes methods for monitoring the level of one or more disease states and/or the efficacy of one or more therapies upon a subject. Suitable subjects include cells, particularly eukaryotic cells, or, more preferably, an organism or an animal, particularly a mammal. In particular, it is often desirable to monitor disease states and/or therapies in a laboratory animal, such as a mouse, which functions as a model for a similar disease or therapy in humans. Alternatively, the methods of the invention may be used for veterinary purposes, i.e., to monitor disease states and/or therapies in animals such as dogs, cats, horses, chickens, cows, etc. In a particularly preferred embodiment, the subject of the invention is a human patient.

The methods involve comparing measurements of the biological state of a cell for which the level (e.g., the stage or progression) of a disease state or the efficacy of a therapy thereto is to be determined with measurements of changes in the biological state of a cell in response to known levels of a disease state or known levels of therapeutic efficacy.

This section first presents certain concepts, including the concepts of biological state and disease state. Next, a schematic and non-limiting overview of the methods of the invention is presented. The following sections present the methods of the invention in greater detail.

Although for simplicity this disclosure often makes references to single cell (e.g., "RNA is isolated from a cell perturbed at a single gene"), it will be understood by those of skill in the art that more often any particular step of the invention will be carried out using a plurality of genetically similar cells, e.g., from a cultured cell line. Such similar cells are called herein a "cell type". Such cells are derived either from naturally single celled organisms, or derived from multi-cellular higher organisms (e.g., human cell lines).

In particular, Section 5.1 describes certain preliminary concepts of the present invention. Section 5.2 generally describes the methods of the invention. Section 5.3 describes a preferred analytic embodiment of the methods of the invention. Section 5.4 describes methods of measuring cellular constituents.

Biological State

The methods of the present invention include methods of measuring and observing the biological state of a cell. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurement relevant to the characterization of drug action. In various embodiments, this invention includes making such measurements and/or observations on different collections of cellular constituents. These different collections of cellular constituents are also called herein aspects of the biological state of the cell.

One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least, a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured to characterize the action of a drug of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and also optionally catalytically active nucleic acid species) in the cell under a given set of conditions. As is known to those of skill in the art, the translational state is often representative of the activity state.

This invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Perturbations in a biological system will affect many constituents of whatever aspects of the biological state of a cell are being measured and/or observed in a particular embodiment of the present invention. In particular, as a result of regulatory, homeostatic, and compensatory networks and systems known to be present in cells, even the direct disruption of only a single constituent in a cell, without directly affecting any other constituent, will have complicated and often unpredictable indirect effects.

The inhibition of a single, hypothetical protein, protein P is considered herein as an example. Although the activity of only protein P is directly disrupted, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. These changes in other cellular constituents can be used to define a "signature" of alterations of particular cellular constituents which are related to the disruption of a given cellular constituent.

Measurement of the transcriptional state of a cell is preferred in this invention, not only because it is relatively easy to measure but also because, even though a protein of interest may not directly modulate transcription, even the slight disruption of protein activity in a cell almost always results in a measurable change, through direct or indirect effects, in the transcriptional state. A reason that disruption in a protein's activity level changes the transcriptional state of a cell is because the previously mentioned feedback systems, or networks, which react in a compensatory manner to infections, genetic modifications, environmental changes, drug administration, and so forth do so primarily by altering patterns of gene expression or transcription. As a result of internal compensations, many perturbations to a biological system, although having only a muted effect on the external behavior of the system, can nevertheless profoundly influence the internal response of individual elements, e.g., gene expression, in the cell.

Disease State

According to the present invention, a disease state refers to any abnormal biological state of a cell. Thus the presence of a disease state may be identified by the same collection of biological constituents used to determine the cell's biological state. In general, a disease state will be detrimental to a biological system.

A disease state may be a consequence of, inter alia, an environmental pathogen, for example a viral infection (e.g., AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., *The Metabolic and Molecular Bases of Inherited Diseases,* 7th ed., McGraw-Hill Inc., New York).

Other exemplary diseases include, but are not limited to, cancer, hypertension, Alzheimer's disease, neurodegenerative diseases, and neuropsychiatric disorders such as bipolar affective disorders or paranoid schizophrenic disorders. Exemplary types of cancer include, but are not limited to, those listed in Table I, below. In a specific embodiment, the disease, the level or progression of which is determined, or for which therapy is monitored according to the invention, is a genetic disease. Thus, in a specific embodiment, the disease is a cancer associated with a genetic mutation, e.g., translocation, deletion, or point mutation (for example, the Philadelphia chromosome).

TABLE I

MALIGNANCIES AND RELATED DISORDERS

Leukemia
    acute leukemia
        acute lymphocytic leukemia
        acute myelocytic leukemia
            myeloblastic
            promyelocytic
            myelomonocytic
            monocytic
            erythroleukemia
    chronic leukemia
        chronic myelocytic (granulocytic) leukemia
        chronic lymphocytic leukemia
Polycythemia vera
Lymphoma
    Hodgkin's disease
    non-Hodgkin's disease
Multiple myeloma
Waldenström's macroglobulinemia
Heavy chain disease
Solid tumors
    sarcomas and carcinomas
        fibrosarcoma
        myxosarcoma
        liposarcoma
        chondrosarcoma
        osteogenic sarcoma
        chordoma
        angiosarcoma
        endotheliosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma TABLE I-continued

MALIGNANCIES AND RELATED DISORDERS choriocarcinoma
        seminoma
        embryonal carcinoma
        Wilms' tumor
        cervical cancer
        uterine cancer
        testicular tumor
        lung carcinoma
        small cell lung carcinoma
        bladder carcinoma
        epithelial carcinoma
        glioma
        astrocytoma
        medulloblastoma
        craniopharyngioma
        ependymoma
        pinealoma
        hemangioblastoma
        acoustic neuroma
        oligodendroglioma
        meningioma
        melanoma
        neuroblastoma
        retinoblastoma In fact, with respect to the present invention, any biological state that is associated with a disease or disorder is considered to be a disease state. As used in the present invention, the "level" of a disease or disease state is an arbitrary measure reflecting the progression or state of a disease or disease state. Generally, a disease or disease state will progress through a plurality of levels or stages, wherein the affects of the disease become increasingly severe.

Accordingly, a therapy or therapeutic regimen, as used herein, refers to a regimen of treatment intended to reduce or eliminate the symptoms of a disease. A therapeutic regimen will typically comprise, e.g., a prescribed dosage of one or more drugs.

Ideally, the effect of a therapy will be beneficial to a biological system in that it will tend to decrease the level of a disease state. However, in many instances, the effect of a therapy will be adverse to a biological system. For example, many therapies, such as drug regimens or chemotherapies, have toxic side effect. In such instances, it is important to monitor adverse effects so that the therapy may be adjusted, e.g., by reducing dosages or terminating the therapy altogether, before the adverse effects become too severe.

In general, a disease or disease state will have particular effects on the constituents of a biological system, i.e., "perturbations". These effects can therefore be correlated to the level of the disease state. In particular, at least at low levels of disease state which comprise low levels of perturbation, individual diseases will generally mediate their effects through different, independent perturbations which can be independently correlated to a particular disease or disease state. Likewise, drugs or other agents which may be used in a therapy will each have unique perturbations on the state of a biological system which can be correlated to the level of efficacy of a particular therapy.

In an alternative embodiment, the methods of the invention can also be used to diagnose or screen for the presence of a disease state.

5.2. Monitoring Disease States and Therapies from Expression Profiles

This section presents, first, an overview of the methods of this invention, and second, an extended illustrative example of the principal of these methods.

Overview of the Methods of this Invention

The methods of this invention determine the level (e.g., the stage or progression) of one or more disease states of a subject and, more specifically, detect changes in the biological state of a subject which are correlated to one or more disease states. The methods of the present invention are also applicable to monitoring the disease state or states of a subject undergoing one or more therapies. Thus, the present invention also provides methods for determining or monitoring efficacy of a therapy or therapies (i.e., determining a level of therapeutic effect) upon a subject. In a specific embodiment, the methods of the invention can be used to assess therapeutic efficacy in a clinical trial, e.g., as an early surrogate marker for success or failure in such a clinical trial.

As used herein, an "expression profile" comprises measurement of a plurality of cellular constituents that indicate aspects of the biological state of a cell. Such measurements may include, e.g., RNA or protein abundances or activity levels.

Aspects of the biological state of a cell of a subject, for example, the transcriptional state, the translational state, or the activity state, are measured as described in Section 5.4. The collection of these measurements, optionally graphically represented, is called herein the "diagnostic profile". Aspects of the biological state of a cell which are similar to those measured in the diagnostic profile, e.g., the transcriptional state, are measured in an analogous subject or subjects in response to a known correlated disease state or, if therapeutic efficacy is being monitored, in response to a known, correlated effect of a therapy. The collection of these measurements, optionally graphically represented, is called herein the "response profile" or "perturbation response profile". The response profiles are interpolated to predict response profiles for all levels of protein activity within the range of protein activity measured. In cases where therapeutic efficacy is to be monitored, the response profile may be correlated to a beneficial effect, an adverse effect, such as a toxic effect, or to both beneficial and adverse effects.

More generally, the methods of the present invention allow one to monitor a plurality of disease states or therapies in an individual subject; for example in a subject having several genetic mutations that are each associated with a particular disease, or in a subject undergoing several therapeutic regimes simultaneously (for example, a patient taking several drugs, each of which has a different effect). Accordingly, response profiles are obtained individually for each disease or therapy.

Cellular constituents in the diagnostic profile are compared to cellular constituents varying in the interpolated perturbation response profiles in order to find a level of disease state or effect of a therapy, for which the perturbation profile matches all or substantially all of the diagnostic profile. If a plurality of disease states or therapies is being monitored, then the diagnostic profile is compared to some combination of the individual perturbation response profiles for each disease or therapy. Substantially all of a diagnostic profile is matched by a response profile when most of the cellular constituents which vary in the response curves are found to have substantially the same value in the two profiles. Preferably, at least 75% of the cellular constituents varying in the response curves can be matched, more preferably at least 90% can be so matched. Cellular constituents have substantially the same value in the two profiles when both sets of data are likely to be the same in view of experimental error.

In a preferred embodiment, comparison of a diagnostic profile with response curves is performed by a method in which an objective measure of difference between a measured diagnostic profile and a perturbation response profile determined for some perturbation level, i.e., for some level of disease or therapeutic efficacy, is minimized. The objective measure is minimized by extracting the perturbation response profile for from the perturbation curves at the perturbation value which minimizes this difference. Minimization of the objective measure can be performed by standard techniques of numerical analysis. See, e.g., Press et al., 1996, *Numerical Recipes in C*, 2nd Ed. Cambridge Univ. Press, Ch. 10.; Branch et al., 1996, *Matlab Optimization Toolbox User's Guide*, Mathworks (Natick, Mass.).

Illustration of the Methods of the Present Invention

Figure 2:
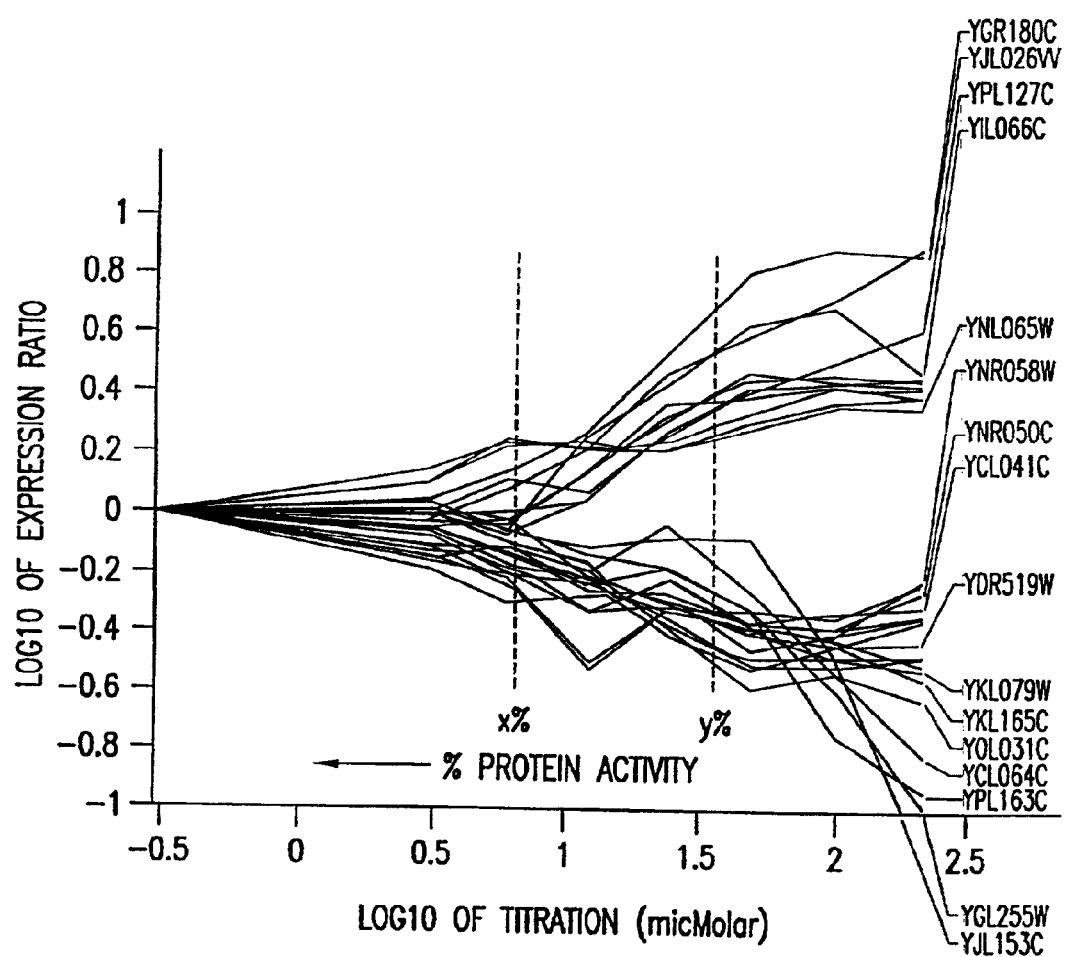

The following paragraphs which generally illustrate several of the methods of the present invention with respect to FIG. 1 and FIG. 2, are presented by way of example but not limitation. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, i.e., a particular disease state or therapy, even at a stage where changes in protein activity are undetectable.

FIG. 1 illustrates an example of a diagnostic profile measured in a deletion mutant of the yeast *Saccharomyces cerevisiae* wherein one of the two (i.e., diploid) copies of the SUN2 gene is disabled. The figure illustrates mRNA expression levels of the approximately 6000 genes in the genome of this yeast. Specifically, the $\log_{10}$ of the ratio of mRNA expression level in the deletion mutant to the expression level in the wild type strain is plotted on the vertical axis, vs. hybridization intensity, which is roughly proportional to molecular abundance, on the horizontal axis. These gene expression level measurements were made with gene transcript arrays, as described in Section 5.4. Genes which were consistently up- or down-regulated in repeated experiments are labeled and flagged with error bars. These error bars indicate the standard deviation in the five repeated measurements for each gene transcript obtained from five microarrays.

Although the SUN2 gene product is not known to be a transcription factor, there are fifteen genes up- or down-regulated by more than a factor of two in response to this heterozygous deletion. Table II, below, shows the $\log_{10}$ of the factor by which the mRNA expression changed for those genes whose expression changed by more than a factor of two. Many of these changes are significantly more than the standard deviation. Measurement of the transcription level of the SUN2 gene itself shows its mRNA expression level is reduced less than a factor of two by the reduction in gene copy number from two to one. Thus, the protein activity level has almost certainly been reduced by less than a factor of two. Nevertheless, there is a distinct response in the expression profile of other genes.

TABLE II

| ORF | Log$_{10}$ (R/G) | +/− StdDev | R/G |
|---|---|---|---|
| YGR065C | −0.31 | 0.03 | 0.48 |
| YKR099W | −0.32 | 0.27 | 0.48 |
| YLR023C | −0.33 | 0.05 | 0.47 |
| YHR096C | −0.35 | 0.05 | 0.47 |
| YMR097C | −0.36 | 0.06 | 0.44 |
| YJR088W | −0.37 | 0.05 | 0.42 |
| YMR011W | −0.4 | 0.12 | 0.4 |
| YKR069W | −0.4 | 0.02 | 0.4 |
| YGL125W | −0.4 | 0.08 | 0.4 |
| YBR105C | −0.41 | 0.12 | 0.39 |
| YDL182W | −0.41 | 0.09 | 0.39 |
| YLR267W | −0.42 | 0.34 | 0.38 |
| YOR383C | −0.47 | 0.34 | 0.34 |
| YGL184C | −0.48 | 0.21 | 0.33 |
| YOR338W | −0.51 | 0.1 | 0.31 |

In fact, such compensatory changes can be monitored long before it is possible to detect changes by monitoring protein function. Thus, by measuring gene expression at different levels of a biological state, and in particular at different levels of a disease state or at different levels of therapeutic efficacy, it is possible to construct response curves that show the effects of a particular disease or therapy long before there is a detectable change in protein function. The resultant up regulation and down regulation of genes within a cell when the biological state of the cell is disrupted or partially disrupted represent compensatory changes that the cell undertakes in order to maintain homeostasis. As these compensatory changes in transcription occur before the cell exhibits any discernable physiological change, these expression profiles are very sensitive indications of the cell's biological state. This sensitivity has a significant value when it comes to diagnosing the presence of a disease state, and also in monitoring the efficacy of a therapy upon a subject having a disease state.

FIG. 2 illustrates an example of perturbation response profiles measured at discrete protein activity levels of dihydrofolate reductase. Specifically, the figure illustrates mRNA expression levels of 30 genes of the yeast *Saccharomyces cerevisiae* that, of the approximately 6000 genes in the genome of this yeast, had the largest expression changes in response to six different titrations of the drug methotrexate, which is known to act primarily by disrupting the activity of dihydrofolate reductase. These gene expression level measurements were made with gene transcript arrays, as described in Section 5.4. The perturbation response profiles in FIG. 2 can be interpolated according to the methods disclosed in Section 5.3, below, to provide perturbation response profiles for any activity level of dihydrofolate reductase, and are thereby correlated to efficacy of the drug methotrexate.

Perturbation response profiles, such as those shown in FIG. 2, can be generated and measured, e.g., by measuring cellular constituents in one or more analogous subjects suffering from the same disease. The perturbation response profiles would then be correlated with the "level" of the disease state, e.g., with progression of the disease state, in the analogous subjects by monitoring the disease state according to traditional methods.

Likewise, perturbation response profiles for monitoring efficacy of a therapy can be generated and measured by measuring cellular constituents in analogous subject or subjects undergoing an identical therapy. The perturbation response profiles are correlated to the efficacy of the therapy by monitoring efficacy of therapy upon the analogous subject using traditional means, e.g., protein function assays.

Passive procedures for obtaining the required gene expression response curves and protein activity data are therefore employed in such systems. Passive procedures for obtaining gene expression response curves and protein activity data include, e.g., taking tissue or blood samples from individuals already undergoing regimens of drug treatment at varying dosages, and also using individuals with known heterozygous mutations for at least one intermediate level of disease state.

In certain embodiments, the "analogous subject" from whom perturbation profiles are obtained may be the same individual (i.e., the same organism or patient) as the subject upon whom a disease state or the effect of a therapy is being monitored. For example, perturbation response profiles may be obtained from an individual having a disease state at one point in time, and then used to monitor the reoccurence of that disease state at some other point in time.

In other embodiments, it is desirable to monitor the effect of a plurality of therapies upon a subject, for example a regimen comprising drugs A, B, and C. In such embodiments, perturbation response profiles could be obtained first for drug A, by monitoring the effect of drug A, alone, on the same subject and correlating that effect with measurements of celular constituents from a cell of that subject. Likewise, perturbation response profiles could next be obtained in the same manner for drug B alone, and for drug C alone. The perturbation response profiles could then be used to monitor the cummulative effect of the combination of therapies (in this example the combination of drugs A, B, and C) upon that same subject.

In still other embodiments, perturbation response profiles are obtained for one or more disease states and/or for one or more drug therapies and are calibrated to a clinical effect or effects. Exemplary clinical effects include, but are not limited to, blood pressure, body temperature, blood or urine glucose levels, cholesterol levels (including, e.g., HDL and LDL levels) viral load levels, blood hematocrit levels, white cell count, tumor size etc. In fact, any measurement of a patient's biochemical and/or physiological state that may be readily obtained in a clinical setting is a measurement of a clinical effect.

In such embodiments, the levels of one or more disease states can be determined and/or monitored in a patient by monitoring the patient's diagnostic profile and comparing it to the clinical effect or effects that are calibrated to perturbation response profiles for the one or more disease states. Likewise, one or more drug therapies may be monitored in a patient by monitoring the diagnostic profile of a patient undergoing the drug therapy (or drug therapies) and comparing it to the clinical effect or effects that are calibrated to perturbation response profiles for the one or more drug therapies. A desirable clinical effect can then be readily achieved for the patient by adjusting the drug therapy (or drug therapies) until the patient's diagnostic profile matches the profile obtained for the desired clinical effect.

Although, much of the description of this invention is directed to measurement and modeling of gene expression data, this invention is equally applicable to measurements of other aspects of the biological state of a cell, such a protein abundances or activities. Methods for direct measurement of protein activity are well known to those of skill in the art. Such methods include, e.g., methods which depend on having an antibody ligand for the protein, such as Western blotting (see, e.g., Burnette, 1981, A. Anal. Biochem. 112: 195–203). Such methods also include enzymatic activity assays, which are available for most well-studied protein drug targets, including, but not limited to, HMG CoA reductase (Thorsness et al., 1989, Mol. Cell. Biol. 9: 5702–5712), and calcineurin (Cyert et al., 1992, Mol. Cell. Biol. 12: 3460–3469). An example of turning off a specific gene function by turning off the controllable promoter, and correlating this with protein depletion via Western blotting is given in Deshaies et al., 1988, Nature 332: 800–805.

The perturbation response curves in FIG. 2 illustrate the generally expected shape of such curves. This expected shape includes a below threshold region of low perturbation control parameter over which there is effectively no response of the cellular constituents to the perturbation. After this below threshold region, the perturbation, i.e., the disease or therapy begins to be efficacious, and the values of characteristics of the cellular constituents are perturbed. The curve of perturbed values is expected to usually have a monotonic increase or decrease toward an asymptotic level at saturation, beyond which no further change is observed. The response curves terminate in this saturation region.

In fact, more complicated, non-monotonic response curve shapes are possible and expected in some situations. For example, in the case where the perturbation has toxic effects, as toxicity sets in rising abundances of cellular constituents may start to fall, and falling abundances may start to fall even faster. Also, nonlinear and feed back mechanisms known to be present in the biological system may result in non-monotonic, multi-phasic responses. Such a response might first increase and then decrease with increasing perturbation amplitude or drug exposure. For example, a perturbation may act on certain cellular constituents through two pathways with different thresholds and with opposite effects to generate increasing and then decreasing (or vice versa) responses.

The methods of this invention are illustrated and primarily described with respect to monotonic response curves, such as those illustrated in FIG. 2. The methods of the invention are primarily applicable to low levels of perturbation to a biological system that occur, e.g., during the early stages of disease. Such perturbations will generally be sufficiently low to avoid levels where toxic effects and/or nonlinearity and feedback effects are observed. Nevertheless, as will be apparent to one of skill in the art, the methods described herein are also applicable to non-monotonic response curves.

5.3. Analytic Embodiments

The analytic embodiments of the methods of the present invention include embodiments for evaluating the difference between a diagnostic profile and a response profile at a particular level of a disease state, or at a particular level of therapeutic efficacy by some objective function. The methods of the invention comprise: determining representative perturbation response profile data for a particular disease state or therapy at a plurality of levels correlated to the particular disease state or therapeutic effect. Diagnostic profile data is then compared with the response profile data from which a level of the disease state and/or a level of therapeutic effect is determined.

In other embodiments of this invention, certain steps may be omitted or performed in orders other than as illustrated. For example, in certain embodiments the step of obtaining perturbation response profile data will already be derived for a certain disease and/or therapy, or for several, preferably related, diseases and/or therapies, and need not be performed separately for each analysis.

5.3.1. Expression Profile Representation

The methods of the present invention preferably begin by measuring perturbation response profiles. In many cases perturbation response profiles will have already been measured for a particular disease state and/or therapy. In other cases, this response data must be measured prior to the succeeding steps of this invention. The measurements are done in analogous subjects, i.e., subjects similar enough to those in whom a level of disease state or therapeutic efficacy is being determined for one skilled in the art to expect that the expression profile will be similar enough to provide useful perturbation response profiles. In a preferred embodiment, the analogous subject is a subject of the same species exhibiting the disease state, and may optionally be of the same sex and/or approximate age.

As described above, the perturbation profiles include measurements of relative changes in relevant characteristics of the cellular constituents correlated to a plurality of known levels (e.g., stages of progression) of a particular disease state and/or to known levels of effect of a particular therapy as observed, e.g., by change in disease symptomology or in a known marker of disease progression or severity. Such markers of disease progression include, for example, alpha-fetoprotein, alkaline phosphatase, calcineurin, inosine monophosphate, etc.

More specifically, the ratios (or logarithms of these ratios) of native (i.e., in the absence of a disease state or therapy) to perturbed (i.e., in the presence of a disease state and/or therapy) gene expression levels are measured.

In the following, the variable "p" refers generally to perturbation levels, which are correlated to levels of a particular disease state or therapeutic effect. The variable "R" refers generally to the perturbation response data. In detail, the l'th perturbation level is referred to as "$p_l$". The perturbation response for the k'th cellular constituent is $R_k$. Therefore, $R_k(p_l)$ is the response of the k'th cellular constituent at the l'th level of perturbation.

Diagnostic profile data are similarly obtained and must be measured if not already available. As described above, the data are obtained by measuring levels of cellular constituents in a cell of interest, i.e., a cell from a subject. The actual level of disease state or therapeutic efficacy is usually unknown when this data is acquired. In the following, the variable "D" refers generally to the diagnostic profile data. In detail, the diagnostic profile for the k'th cellular constituent is $D_k$. Typically, the values of $R_k(p)$ and $D_k$ are $\log_{10}$ of the expression ratio of each cellular constituent. The expression ratio is the ratio between the level in the perturbed system, and the level in the native system.

In general, the actual level at which diagnostic profile data are acquired will not correspond to any of the perturbation levels at which perturbation response profiles are actually acquired. Accordingly, it is necessary to provide for interpolating of the perturbation response data to obtain needed values. This interpolation method is preferably accomplished either by spline fitting or by model-fitting. The selection of an interpolation method and any necessary parameters is accomplished in step 303.

In spline fitting, the perturbation response data are interpolated by summing products of an appropriate spline interpolation function, S, multiplied by the measured data values, as illustrated by the following equation.

$$R_k(u) = \sum_l S(u - p_l) R_k(p_l) \qquad (1)$$

The variable "u" refers to an arbitrary level of disease or therapeutic efficacy at which the perturbation response data are to be evaluated. In general, S may be any smooth, or at least piece-wise continuous, function of limited support having a width characteristic of the structure expected in the response functions. An exemplary width can be chosen to be the distance over which the response function being interpolated rises from 10% to 90% of its asymptotic value. Exemplary S functions include linear and Gaussian interpolation.

In model fitting, the perturbation responses are interpolated by approximating each by a single parameterized function. An exemplary model-fitting function appropriate for approximating transcriptional state data is the Hill function, which has adjustable parameters a, $u_0$, and n.

$$H(u) = \frac{a(u/u_0)^n}{1+(u/u_0)^n} \quad (2)$$

the adjustable parameters are selected independently for each cellular constituent of the perturbation response. Preferably, the adjustable parameters are selected so that for each cellular constituent the sum of the squares of the distances $H(p_l)$ from $R_k(P_l)$ is minimized. This preferable parameter adjustment method is known in the art as a least squares fit of $H(\ )$ to $R_k(\ )$. Other possible model functions are based on polynomial fitting, for example by various known classes of polynomials.

Figure 3:
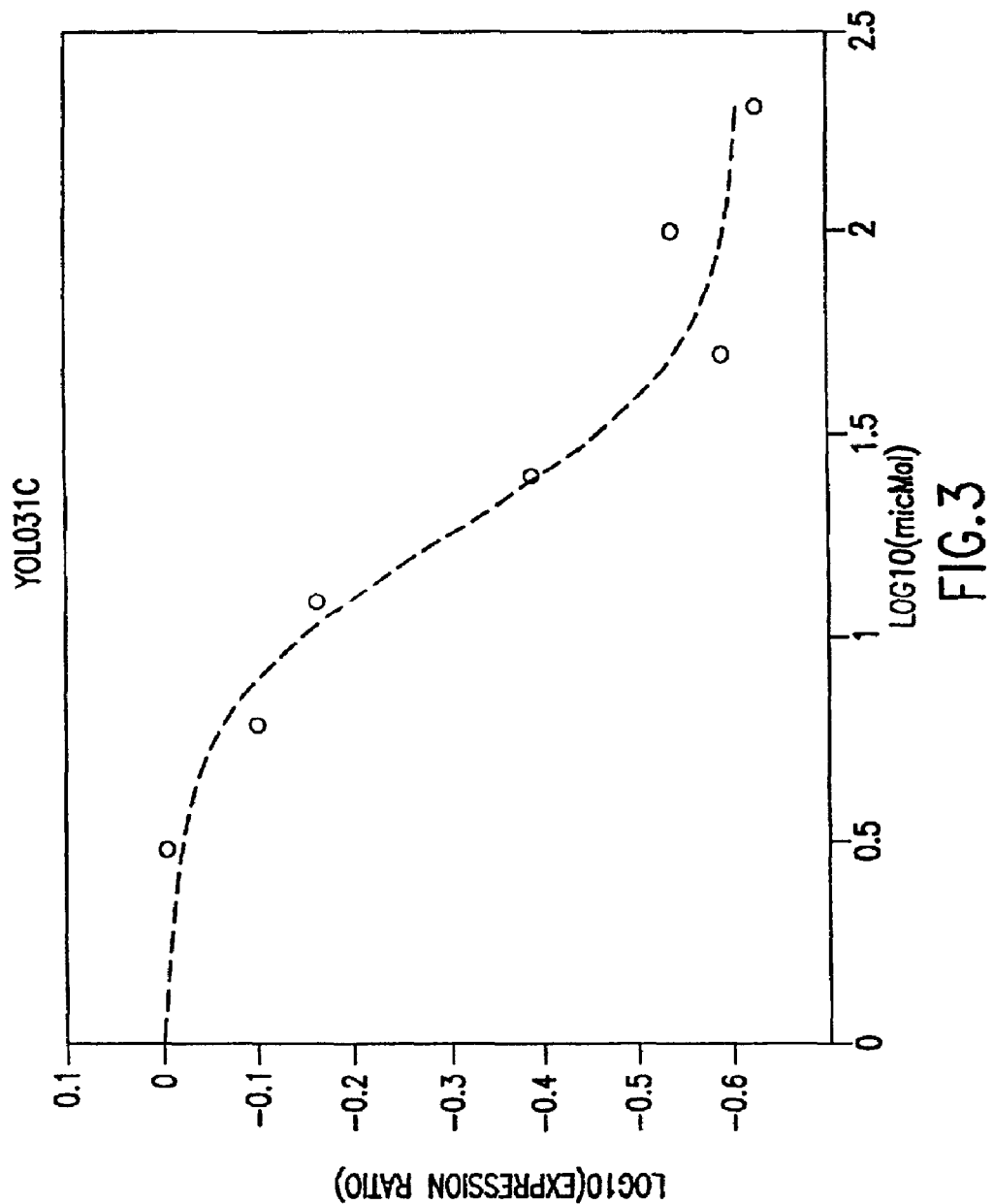
FIG. 3 illustrates the fit of a Hill function to the response of gene YOL031C illustrated in FIG. 2.

Model fitting with a Hill function is illustrated with respect to FIGS. 2 and 3. As discussed, FIG. 2 illustrates an example of perturbation by methotrexate and identified by measurement. This figure illustrates the RNA expression levels of 30 genes of the yeast S. cerevisiae that, of the approximately 6000 genes in the genome of this organism, had the largest expression changes in response to six different exposure levels of methotrexate. FIG. 3 illustrates a fit of the perturbation response of one of these gene expression levels by a Hill function. In particular, the yeast gene YOL031C was fit by a Hill function with parameters n=2, a=-0.61, and $\log_{10}(u_0)$=1.26 selected by the previously described least squares method.

Since all of the 30 genes with largest responses behaved monotonically, i.e., none of the responses decreased significantly from its maximum amplitude (or increased significantly from its minimum amplitude) with increasing drug exposure, the Hill function is an appropriate model fitting function. For non-monotonic behavior it would not be.

Given the interpolation of the perturbation responses to any level of perturbation, denoted p, the diagnostic expression profile D can be compared with the perturbation response curves R(p) to find the best-fit over all possible values of p. According to one preferred method, the best-fit over all possible values of p is determined from the minimization of the related least squares approximation problem.

$$\min_{\{p\}} \left\{ \sum_k \left( (D_k - R_k)(p) \right)^2 \right\} \quad (3)$$

In Eqn. 3, the absolute square of the difference of the interpolated response profile and the diagnostic profile is summed over all cellular constituents in the profiles, indexed by "k". The best-fit of the diagnostic profile in terms of the response curves is determined from the minimization of this sum with respect to the protein activity level p. Minimization of least squares Eqn. 3 is performed using any of the many available numerical methods. See, e.g., Press et al., 1996, *Numerical Recipes in C*, 2nd Ed. Cambridge Univ. Press, Chs. 10, 14.; Branch et al., 1996, *Matlab Optimization Toolbox User's Guide*, Mathworks (Natick, Mass.).

Typically, there will be some variation from experiment to nominally repeated experiment in the asymptotic value of the responses. Individual cellular constituents have similar relative response amplitudes in repeated experiment, but all responses may be systematically larger or smaller in one experiment. This can cause the value of p determined in Eqn. 3 to be biased high or low. An alternative fitting approach which prevents these systematic amplitude discrepancies from biasing the derived p is to maximize the correlation between the response profile and the diagnostic profile. This procedure is closely related mathematically to the least squares procedure. According to this procedure, the protein activity level p is determined from the solution to Eqn. 4.

$$\max_{\{p\}} \left\{ \frac{\sum_k R_k(p) D_k}{\left[ \left( \sum_k R_k^2(p) \right) \left( \sum_k D_k^2 \right) \right]^{1/2}} \right\} \quad (4)$$

Eqn. 4 can be solved by the methods described in the case of the least squares methods. It will be clear to those skilled in the art that the above fitting approach is equivalent to minimizing the negative value of Eqn. 4.

In certain instances, Eqn. 4 will have a very shallow, and hence poorly determined maximum location. Specifically, in many cases the response profiles R(p) will look very similar at different p except for an over-all scaling with increasing p. In these cases, the best-fit over all possible values of p is preferably determined by the least-squares method in Eqn. 3. In instances where the relative response amplitudes of different cellular constituents change significantly with changing levels of disease state or therapeutic effect, e.g., that generate response curves like those illustrated in FIG. 2, the best-fit over all possible values of p is preferably determined by maximizing Eqn. 4.

In certain embodiments, the methods of the invention can be used to monitor the level of a plurality of disease states simultaneously, or to simultaneously monitor the efficacy of a plurality of therapies. In such embodiments, the perturbation response, $R_{i,k}(P_{i,l})$ of the k'th cellular constituent at the l'th perturbation level is seperately determined for the i'th disease state or therapy. The response profiles for each disease are interpolated, as described above, to generate an interpolated response profile for each disease state or therapy, $R_{i,k}(p_i)$. The diagnostic expression profile D can then be compared to a combination of the perturbation response curves $R_i(p_i)$ for each disease state or therapy to find a best-fit over all possible values of $\{p_i\}$. In a particularly preferred embodiment, the effects of therapies and/or the levels of diseases are sufficiently low the nonlinear or feed back effects, discussed above, are not observed. In such an embodiment, the perturbation response profile may simply be compared to the sum of perturbation response curves for each disease, i.e., to $\Sigma R_i(p_i)$. Accordingly, in embodiments where the best fit is determined by minimization of the least squares problem, the best fit is the solutaion to Equation 5.

$$\min_{\{p_i\}} \left\{ \sum_k \left( D_k - \sum_i R_{i,k}(p_i) \right)^2 \right\} \quad (5)$$

5.3.2. Assessing Statistical

Following the extraction of a perturbation response profile or profiles which best fit the diagnostic profile, it is preferable, although optional, in certain embodiments to assign a statistical significance to the corresponding fit.

The statistical significance of the fit of the response profiles to the diagnostic profile is determined by comparing the value of the minimum residual determined from the solution of Eqn. 3 or 5 to an expected probability distribution of residuals. The less likely the minimum residual is in terms of such a distribution, the more significant is the corresponding fit. In the case of the correlation maximization method, the same methods can be applied to the maximum found in Eqn. 4. In particular, an expected distribution of maximums can be found (as described below), and the significance of the actually obtained maximum determined from this distribution.

An expected probability distribution of residuals can be estimated by any method known in the art. Typically, this distribution is estimated analytically based on certain a priori assumptions concerning input probability distributions. Since such analytic estimation is difficult in this case, it is preferable to estimate the residual distribution by modeling based on a method described by Fisher. See, e.g., Conover, 2nd ed. 1980, *Practical Nonparametric Statistics*, John Wiley. This method provides an empirical residual distribution by taking permutations or random subsets of the input data. In detail, here the input can be permuted with respect to the cellular constituents measured in the diagnostic profile.

According to the preferred method, a residual distribution is constructed by repetitively solving Eqn. 5 (or Eqn. 4) with randomized input data and accumulating the residuals to form the empirical residual distribution. Thereby, the constructed empirical residual distribution arises from random data that has the same population statistics as the actual data. In detail, first, either the diagnostic profile data or the response profile data (but not both) are randomized with respect to the cellular constituent index. This randomization transformation is represented by the following transformation.

$$D_k \leftarrow D_{\Pi(k)} \quad (6)$$
$$R_{i,k}(p_{i,l}) \leftarrow R_{i,\Pi(k)}(p_{i,l})$$

In Eqn. 6, $\Pi$ represents a perturbation independently chosen for each profile. Either the diagnostic profile or each response profile (but not both) is randomized according to Eqn. 6. Accordingly, the randomized expression profile data are derived from the measured data by independent permutations of the measurement points. Second, Eqn. 5 (or Eqn. 4) is then solved by the chosen numerical approximation technique and the value of the resulting residual saved. These steps are repeated for enough randomizations to construct a sufficiently significant expected probability distribution of residuals. In order to obtain confidence levels of 99% or better (i.e., a P-value less than 0.01), then more than 100 randomizations are needed.

Having constructed the empirical residual distribution, the actually determined residual is compared to the constructed distribution, and its probability determined in view of that distribution. This probability is the significance assigned to the fit of the extracted response profile to the diagnostic profile. In other words, the statistical significance of any fit of a combination of cellular constituents to the diagnostic profile is given in the preferred embodiment by the smallness of the probability value that randomized data are fit better by the assumed level of disease state or of therapeutic effect than the actual data.

In cases wherein the fit has at least the standard 95% probability threshold commonly used in medical sciences, the corresponding disease or therapeutic efficacy level can then be considered to have adequate statistical significance. In other cases, an acceptable significance threshold may not be met. If so, then in certain embodiments it can be advantageous to select new perturbation profile data in order to find a response profile which fits the diagnostic profile with the chosen threshold of significance.

For example, in embodiments of this invention wherein the methods are used to diagnose or monitor individuals having a particular disease or disease state, the perturbation response profile data frequently consists of expression profile data from individuals having known perturbations due to the particular disease state or level thereof. In such embodiments, it is preferable to assign a statistical significance to the fit of the perturbation response profile for the known perturbations to the diagnostic profile of an uncharacterized individual. In cases wherein the fit has at least the standard 95% probability threshold commonly used in medical sciences, the individual can then be diagnosed as having the corresponding disease. Alternatively, if the fit does not have at least 95% significance, a statistical significance may be assigned to fits of one or more other perturbation response profiles to the diagnostic profile, using perturbation response profiles obtained from individuals having other, different, known disease states or levels thereof until a perturbation response profile is identified which does have at least 95% significance.

5.3.3. Implementation Systems and Methods

Figure 4:
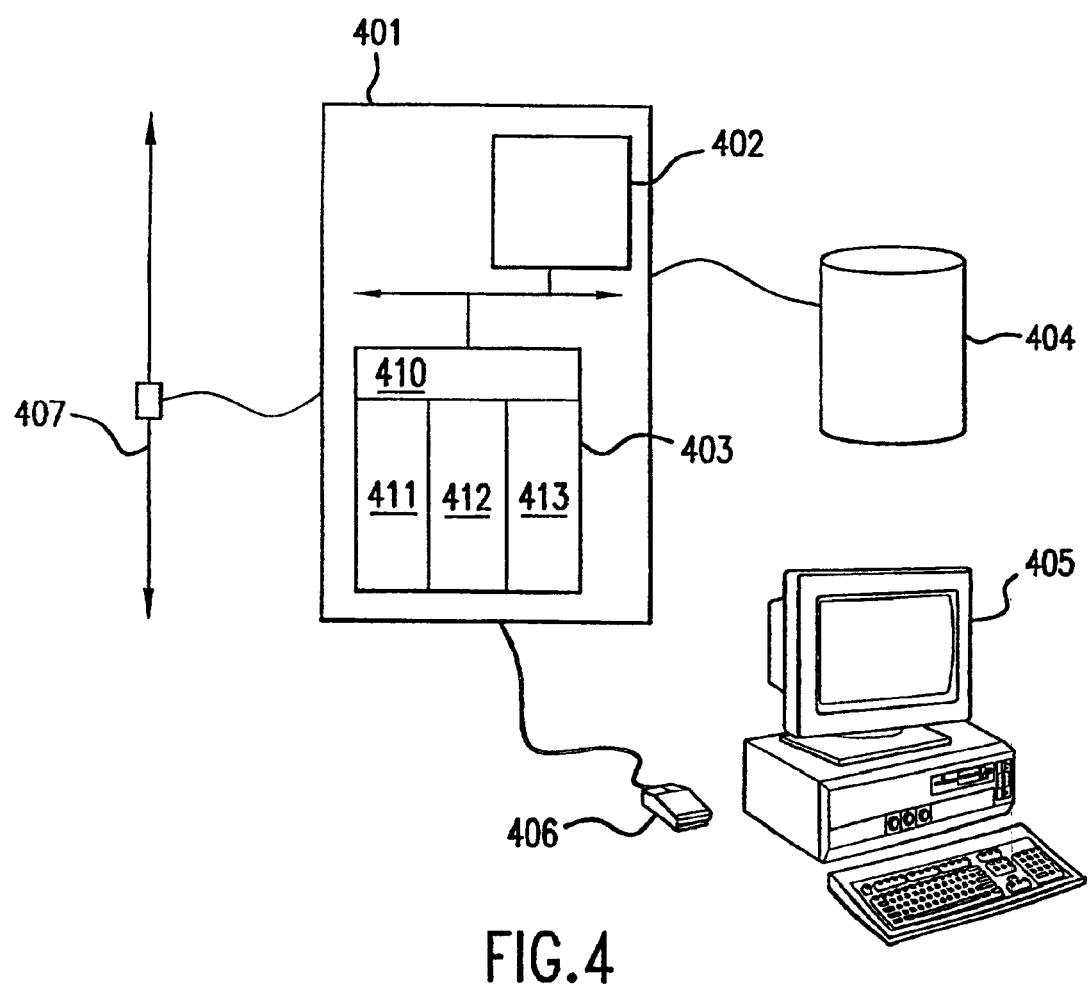
FIG. 4 illustrates an exemplary embodiment of a computer system of this invention.

The analytic methods described in the previous subsections can preferably be implemented by use of the following computer systems and according to the following programs and methods. FIG. 4 illustrates an exemplary computer system suitable for implementation of the analytic methods of this invention. Computer system 401 is illustrated as comprising internal components and being linked to external components. The internal components of this computer system include processor element 402 interconnected with main memory 403. For example, computer system 401 can be an Intel Pentium®-based processor of 200 Mhz or greater clock rate and with 32 MB or more of main memory.

The external components include mass storage 404. This mass storage can be one or more hard disks (which are typically packaged together with the processor and memory). Such hard disks are typically of 1 GB or greater storage capacity. Other external components include user interface device 405, which can be a monitor and keyboard, together with pointing device 406, which can be a "mouse", or other graphic input devices (not illustrated). Typically, computer system 401 is also linked to network link 407, which can be part of an Ethernet link to other local computer systems, remote computer systems, or wide area communication networks, such as the Internet. This network link allows computer system 401 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 404. Software component 410 represents the operating system, which is responsible for managing computer system 401 and its network interconnections. This operating system can be, for example, of the Microsoft Windows™ family, such as Windows 95, Windows 98, or Windows NT. Software component 411 represents common languages and functions conveniently present on this system to assist programs implementing the methods specific to this invention. Languages that can be used to program the analytic methods of this invention include C and C++, or, less preferably, JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Seattle, Wash.). Accordingly, software component 412 represents the analytic methods of this invention as programmed in a procedural language or symbolic package. In a preferred embodiment, the computer system also contains a database 413 of perturbation response profiles for a particular disease or therapy. More preferably, the database 413 contains perturbation response profiles for several diseases and/or therapies.

In an exemplary implementation, to practice the methods of the present invention, a user first loads diagnostic profile data into the computer system 401. These data can be directly entered by the user from monitor and keyboard 405, or from other computer systems linked by network connection 407, or on removable storage media such as a CD-ROM or floppy disk (not illustrated). Next the user causes execution of expression profile analysis software 412 which performs the steps of determining and minimizing an objective function of the difference between the diagnostic profile and a response profile determined from the perturbation response profile data for some level of disease state or therapeutic effect. In a less preferable embodiment, the user loads perturbation response profile data and the steps of interpolating the response profile data are performed by the analysis software 412.

The present invention also provides databases of perturbation response profiles for use in disease states and/or therapies according to the methods of this invention. The databases of this invention include perturbation response profiles for a disease or therapy, preferably for several different diseases and/or therapies so that the same database may be used to monitor several different diseases and/or therapies. Preferably, such a database will be in an electronic form that can be loaded into a computer system such as the one illustrated in FIG. 4 and described supra. Such electronic forms include databases loaded into the main memory 403 of a computer system used to implement the methods of this invention, or in the main memory of other computers linked by network connection 407, or on mass storage media 404, or on removable storage media such as a CD-ROM or floppy disk.

In a preferred embodiment, the analytic methods of this invention can be implemented by use of kits for determining the activity level of a particular protein in a cell. Such kits contain arrays or microarrays, such as those described in Subsection 5.4.1, below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations correlated to the particular diseases or therapies to be monitored by the kit. The probes contained in the kits of this invention preferably substantially exclude nucleic acids which hybridize to RNA species that are not increased or decreased in response to perturbations correlated to the particular levels of disease states or therapeutic effects to be determined by the kit.

In a preferred embodiment, a kit of the invention also contains a database of perturbation response profiles such as the databases described above in this subsection.

In another preferred embodiment, a kit of the invention further contains expression profile analysis software capable of being loaded into the memory of a computer system such as the one described supra in the subsection, and illustrated in FIG. 4. The expression profile analysis software contained in the kit of this invention, is essentially identical to the expression profile analysis software 412 described above. Such software is capable of executing the analytical steps of the present invention. Preferably, the software causes the processor of a computer system to execute the steps of (a) receiving a diagnostic profile of a cell of a subject, (b) receiving perturbation response profiles correlated to levels of a particular disease state or effect of therapy, and (c) determining the interpolated response profile at which similarity is greatest between said diagnostic profile and the determined interpolated perturbation response profile.

Alternative systems and methods for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

5.4. Measurement Methods

Diagnostic and perturbation response profiles are obtained for use in the instant invention by measuring the cellular constituents changed by perturbation of the biological state of the cell, e.g., by diseases or therapies. These cellular characteristics can be of any aspect of the biological state of a cell. They can be of the transcriptional state, in which RNA abundances are measured, the translation state, in which protein abundances are measured, the activity state, in which protein activities are measured. The cellular characteristics can also be of mixed aspects, for example, in which the activities of one or more proteins are measured along with the RNA abundances (gene expressions) of cellular constituents. This section describes exemplary methods for measuring the cellular constituents affected by disrupted or perturbed biological states. This invention is adaptable to other methods of such measurement.

Embodiments of this invention based on measuring the transcriptional state of a cell are preferred. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates). Such measurement methods are described in Section 5.4.1.

In various alternative embodiments of the present invention, aspects of the biological state other than the transcriptional state, such as the translational state, the activity state, or mixed aspects can be measured. Details of such measurement methods are described in Section 5.4.2.

5.4.1. Transcriptional State Measurement

Preferably, measurement of the transcriptional state is made by hybridization to transcript arrays, which are described in this subsection. Certain other methods of transcriptional state measurement are described later in this subsection.

Transcript Arrays Generally

In a preferred embodiment the present invention makes use of "transcript arrays" (also called herein "microarrays"). Transcript arrays can be employed for analyzing the transcriptional state in a cell, and especially for measuring the transcriptional states of cells exposed to graded levels of a therapy of interest such as graded levels of a drug of interest or to graded levels of a disease state of interest.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of therapeutic efficacy (e.g., in response to drugs) one cell is exposed to a therapy and another cell of the same type is not exposed to the therapy. In the case of disease states one cell exhibits a particular level of disease state and another cell of the same type does not exhibit the disease state (or the level thereof). The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the therapy-exposed (or diseased) cell will fluoresce green when the fluorophore is stimulated and the cDNA from the untreated cell will fluoresce red. As a result, when the therapy has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the therapy-exposed cell is treated with a therapy that, directly or indirectly, increases the prevalence of the mRNA in the cell, the ratio of green to red fluorescence will increase. When the therapy decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, *Science* 270: 467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a therapy-exposed or diseased cell and an untreated or nondiseased cell.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, *Science* 274: 546–567, which is incorporated by reference in its entirety for all purposes). In contrast, the human genome is estimated to contain approximately 105 genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., *Oligo* version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, *PCR Protocols: A Guide to Methods and Applications*, Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14: 5399–5407; McBride et al., 1983, *Tetrahedron Lett.* 24: 245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365: 566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29: 207–209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270: 467–470. This method is especially useful for preparing microarrays of cDNA. See also DeRisi et al., 1996, Use of a cDNA microarray to analyze gene expression patterns in human cancer, *Nature Genetics* 14: 457–460; Shalon et al., 1996, A DNA microarray system for analyzing complex DNA samples using two-color fluorescent probe hybridization, *Genome Res.* 6: 639–645; and Schena et al., 1995, Parallel human genome analysis; microarray-based expression of 1000 genes, *Proc. Natl. Acad. Sci. USA* 93: 10539–11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251: 767–773; Pease et al., 1994, Light-directed oligonucleotide arrays for rapid DNA sequence analysis, *Proc. Natl. Acad. Sci. USA* 91: 5022–5026; Lockhart et al., 1996, Expression monitoring by hybridization to high-density oligonucleotide arrays, *Nature Biotech* 14: 1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bioelectronics* 11: 687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs. Another preferred method of making microarrays is by use of an inkjet printing process to synthesize oligonucleotides directly on a solid phase, as described, e.g., in copending U.S. patent application Ser. No. 09/008,120 filed on Jan. 16, 1998 by Blanchard entitled "Chemical Synthesis Using Solvent Microdroplets", which is incorporated by reference herein in its entirety.

Other methods for making microarrays, e.g., by masking (Maskos and Southern, 1992, *Nuc. Acids Res.* 20: 1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly(A)$^+$ RNA are well known and are described generally in Sambrook et al., supra.

In one embodiment, RNA is extracted from cells of the various types of interest in this invention using guanidinium thiocyanate lysis followed by CsCl centrifugation (Chirgwin et al., 1979, *Biochemistry* 18: 5294–5299). Poly(A)$^+$ RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see e.g., Klug and Berger, 1987, *Methods Enzymol.* 152: 316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, *Nature Biotech.* 14: 1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, *Gene* 156: 207; Pietu et al., 1996, Novel gene transcripts preferentially expressed in human muscles revealed by quantitative hybridization of a high density cDNA array, *Genome Res.* 6: 492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™ II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5×SSC plus 0.2% SDS at 65° C. for 4 hours followed by washes at 25 C. in low stringency wash buffer (1×SSC plus 0.2% SDS) followed by 10 minutes at 25° C. in high stringency wash buffer (0.1×SSC plus 0.2% SDS) (Shena et al., 1996, *Proc. Natl. Acad. Sci. USA*, 93: 10614). Useful hybridization conditions are also provided in, e.g., Tijessen, 1993, *Hybridization With Nucleic Acid Probes*, Elsevier Science Publishers B.V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, *Genome Research* 6: 639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, *Genome Res.* 6: 639–645 and in other references cited herein. Alternatively, the fiber-optic bundle described by Ferguson et al., 1996, *Nature Biotech.* 14: 1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

Measurement of Response Profiles

In one embodiment of the invention, transcript arrays reflecting the transcriptional state of a cell of interest are made by hybridizing a mixture of two differently labeled probes each corresponding (i.e., complementary) to the mRNA of a different cell of interest, to the microarray. According to the present invention, the two cells are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed).

In order to measure response profiles, cells are prepared or grown that have graded levels of disease state or of therapeutic effect of interest (i.e., "the perturbation"). The cells having the perturbation and cells not having the perturbation are used to construct transcript arrays, which are measured to find the mRNAs with modified expression and the degree of modification due to the level of disease state or level of therapeutic effect. Thereby, the response profile is obtained.

The density of levels of the graded perturbation control parameter is governed by the sharpness and structure in the individual gene responses—the steeper the steepest part of the response, the denser the levels needed to properly resolve the response. This exemplary density is approximately indicated by the example of FIG. 2. There, six exposures to methotrexate over a hundred-fold range of concentrations were just sufficient to resolve the gene expression responses. However, more exposures are preferable to more finely represent this pathway.

Further, it is preferable, in order to reduce experimental error, to reverse the fluorescent labels in two-color differential hybridization experiments to reduce biases peculiar to individual genes or array spot locations. In other words, it is preferable to first measure gene expression with one labeling (e.g., labeling perturbed cells with a first fluorochrome and unperturbed cells with a second fluorochrome) of the mRNA from the two cells being measured, and then to measure gene expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a trade-off may be made when choosing the width of the spline function S used to interpolate response data between averaging of errors and loss of structure in the response functions.

Measurement of Diagnostic Profiles

Diagnostic profiles may be obtained for any cell type in which it may be desirable to analyze the level of some disease state or of some therapeutic effect. Preferably, the disease state or therapy must be one for which response profiles are either already available, or can be generated. Cells for which it may be desirable to obtain diagnostic profiles include, for example, cells of a patient suspected of having a level of a disease state associated with one or more genetic mutations, as well as cells of a patient which has been exposed to a drug or a combination of drugs or other therapies and which exhibit a level of therapeutic effect.

To measure diagnostic profiles of cells suspected of having a particular level of a disease state or therapeutic effect, cells suspected of having such a level and wild type cells of the same cell type (i.e., cells not having the disease state and/or not exposed to the therapy) are used to construct transcript arrays, which are measured to find the mRNAs with altered expression due to the level of disease state or therapeutic effect. Thereby, the diagnostic profile is obtained.

To measure diagnostic profiles, e.g., of cells exposed to a drug (or to some other therapy), the cells, or the organism/patient from which the cells are obtained, are exposed to some level of the drug of interest, preferably a level corresponding to clinical dosages of the drug, and a measure of therapeutic effect is taken (e.g., measuring change in amount of a disease marker or disease symptom). When the cells are grown in vitro, the drug is usually added to their nutrient medium. In the case of yeast, it is preferable to harvest the yeast in early log phase, since expression patterns are relatively insensitive to time of harvest at that time. The drug is added is a graded amount that depends on the particular characteristics of the drug, but in cell cultures will usually be between about 1 ng/ml and 100 mg/ml. In some cases a drug will be solubilized in a solvent such as DMSO.

The cells exposed to therapy or having a disease state and cells not exposed to therapy and/or not having a disease state (or the particular level of disease state) are used to construct transcript arrays, which are measured to find the mRNAs with altered expression due to the level of disease state or therapeutic effect. Thereby, the response profile is obtained.

Similarly for measurements of response profiles, it is preferable also for diagnostic profiles, in the case of two-color differential hybridization, to measure also with reversed labeling.

Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93: 659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270: 484–487).

5.4.2 Measurement of Other Aspects of Biological State

In various embodiments of the present invention, aspects of the biological state other than the transcriptional state, such as the translational state, the activity state, or mixed aspects can be measured in order to obtain therapy and disease state responses. Details of these embodiments are described in this section.

Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a disease state or therapeutic effect of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array. and their binding is assayed with assays known in the art.

Alternatively, proteins can be separated by two-dimensional gel electrophoresis systems Two-dimensional gel electrophoresis is well-known in the art and typically involves iso-electric focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al., 1996, *Proc. Nat'l Acad. Sci. USA* 93: 1440–1445; Sagliocco et al., 1996, *Yeast* 12: 1519–1533; Lander, 1996, *Science* 274: 536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for diagnosing a level of a disease state of a subject, said method comprising
   (1) determining, for said disease state, an interpolated response profile for which similarity is greatest between a diagnostic profile and said determined interpolated response profile, said diagnostic profile comprising measurements of a first plurality of cellular constituents in one or more cells of said subject, and said determined interpolated response profile comprising measurements of a second plurality of cellular constituents comprising at least a portion of said first plurality, each said measurement being extracted from an interpolate response curve of said measurement as a function of level of said disease state, wherein said interpolated response curve is obtained by a method comprising
      (i) providing response profiles of one or more cells of one or more analogous subjects for said disease state, wherein each of said response profiles comprises measurements of said second plurality of cellular constituents in one or more cells of one of said one or more analogous subjects at one of a plurality of levels of said disease state, and
      (ii) interpolating measurements of each said cellular constituent in said response profiles over said plurality of levels of said disease state to generate an interpolated response curve so that an interpolated response profile comprising measurements of said portion of said first plurality of cellular constituents at a same level of said disease state may be extracted over a range of levels of said disease state,
   wherein the level of disease state correlated to said determined interpolated response profile indicates said level of said disease state of said subject;
   (2) determining statistical significance of said similarity between said determined interpolated response profile and said diagnostic profile; and
   (3) diagnosing said patient as having said level of said disease correlated to said determined interpolated response profile if said statistical significance is at least 95%.

2. The method of claim 1, wherein said determined interpolated response profile yields a maximum correlation between said diagnostic profile and said determined interpolated response profile.

3. The method of claim 2, wherein said statistical significance is determined by comparing the value of said maximum correlation to an expected probability distribution of values of maximum correlation.

4. The method of claim 3, wherein said expected probability distribution of values of maximum correlation is obtained by a method comprising
   (a) randomizing said diagnostic profile data with respect to cellular constituents to generate a permuted diagnostic profile;
   (b) obtaining an interpolated response profile, said interpolated response profile yielding a maximum correlation between said permuted diagnostic profile and said interpolated response profile; and
   (c) repeating steps (a) and (b) to construct a probability distribution of values of maximum correlation.

5. The method of claim 3, wherein said expected probability distribution of values of maximum correlation is obtained by a method comprising
   (a) randomizing said response profile data with respect to the cellular constituents to generate permuted interpolated response curves;
   (b) obtaining an interpolated response profile, said interpolated response profile being extracted from said permuted interpolated response curves and yielding a maximum correlation between said diagnostic profile and said interpolated response profile; and
   (c) repeating steps (a) and (b) to construct a probability distribution of values of maximum correlation.

6. The method of claim 1, wherein said determined interpolated response profile yields a minimum difference between said diagnostic profile and said determined interpolated response profile.

7. The method of claim 6, wherein said statistical significance is determined by comparing the value of the minimum difference to an expected probability distribution of values of minimum difference.

8. The method of claim 7, wherein said expected probability distribution of values of minimum difference is obtained by a method comprising
  (a) randomizing said diagnostic profile data with respect to the cellular constituents to generate a permuted diagnostic profile;
  (b) obtaining an interpolated response profile, said interpolated response profile yielding a minimum difference between said permuted diagnostic profile and said interpolated response profile; and
  (c) repeating steps (a) and (b) to construct a probability distribution of values of minimum difference.

9. The method of claim 7, wherein said expected probability distribution of values of minimum difference is obtained by a method comprising
  (a) randomizing said response profile data with respect to the cellular constituents to generated permuted interpolated response curves;
  (b) obtaining an interpolated response profile, said interpolated response profile being extracted from said permuted interpolated response curves and yielding a minimum difference between said diagnostic profile and said interpolated response profile; and
  (c) repeating steps (a) and (b) to construct a probability distribution of values of minimum difference.

* * * * *